United States Patent [19]

Carol

[11] Patent Number: 4,805,615

[45] Date of Patent: Feb. 21, 1989

[54] METHOD AND APPARATUS FOR PERFORMING STEREOTACTIC SURGERY

[76] Inventor: Mark P. Carol, P.O. Box 748, Cooperstown, N.Y. 13326

[21] Appl. No.: 751,213

[22] Filed: Jul. 2, 1985

[51] Int. Cl.$^4$ ............................................. A61B 17/00
[52] U.S. Cl. ................................. 128/303 B; 403/90; 403/115; 403/131
[58] Field of Search .............. 128/303 B; 403/90, 114, 403/115, 131

[56] References Cited

U.S. PATENT DOCUMENTS

| | | | |
|---|---|---|---|
| 3,016,899 | 1/1962 | Stenvall | 604/175 |
| 3,017,887 | 1/1962 | Heyer | 604/175 |
| 3,021,842 | 2/1962 | Flood | 604/175 |
| 4,058,114 | 11/1977 | Soldner | 128/754 |
| 4,228,799 | 10/1980 | Anichkov et al. | 128/303 B |
| 4,386,602 | 6/1983 | Sheldon et al. | 128/303 B |
| 4,602,622 | 7/1986 | Bar et al. | 128/303 B |
| 4,608,977 | 9/1986 | Brown | 128/303 B |
| 4,638,798 | 1/1987 | Shelden et al. | 128/303 B |

OTHER PUBLICATIONS

"Instruction Manual for the BRW Brown-Roberts-Wells CT Stereotaxic System"; 1983, Radionics, Inc., by Peter Heilbrown & Theodore Roberts, 31 pages.
"Todd-Wells Manuel of Stereotaxic Procedures", Edwin M. Todd, M.D. 1967, 8 pages, San Marino Neurological Center, San Marino, Calif.
"The PMT ® Vaxiom TM Stereotactic System"; 1983, PMT Corporation, Hopkins, Minn., 4 pages.
"Technical Sheet #21"; 1983, DAP II Brain Biopsy Needle Guide; Ad-Tech Medical Instrument Corporation, 9 pages.
"Wells Stereotaxic Guides"; Rand-Wells Palhdothalamectomy Guide; 1 page; undated.
"A Plastic Ball-And-Socket Type of Stereotactic Director"; 1958; George Austin, M.D. and Arnold Lee, A.B., 4 pages.
"Simple Plastic Stereotactic Unit for Use in the Computed Tomographic Scanner"; 1983; Walter J. Levy, M.D., Neuro Surgery, vol. 13, No. 2, 3 pages.

Primary Examiner—Carroll B. Dority, Jr.
Attorney, Agent, or Firm—Ben D. Tobor

[57] ABSTRACT

A method and apparatus for performing stereotactic surgery upon a target within a skull establishes a first, predetermined geometric relationship between a positioning fixture mounted on the skull and a scanning table surface upon which the skull is supported; and that geometric relationship is duplicated in a phantom fixture.

35 Claims, 7 Drawing Sheets

METHOD AND APPARATUS FOR PERFORMING STEREOTACTIC SURGERY

FIELD OF THE INVENTION

The invention relates to a method and apparatus for performing stereotactic surgery with a medical instrument upon a target within a skull.

DESCRIPTION OF THE PRIOR ART

One of the ongoing interests of neurosurgeons is the practice of stereotactic surgery: gaining precise access to a specific point in the cranium through the application of an external three-dimensional coordinate system. Much time and effort has gone into the development of instrumentation for implementing such an approach to the human brain. With the development of computerized tomographic ("CT") scanning, and its precise imaging, stereotactic surgery is becoming the diagnostic and therapeutic procedure of choice for many disorders involving the intracranial cavity.

CT scanning produces an image representing a "slice" of brain tissue displayed with anatomical accuracy. The series of "slices", which constitute the complete CT study, represent a three-dimensional picture of the brain, defining the relationship of neurological structures or accurately localizing lesions. CT scanning has allowed physicians to visualize the brain directly, thus making identification of anatomical and pathological areas of interest much more precise, and thus much more accessible to the precise mechanics of stereotactic surgery. Mating CT scanning and stereotactic surgery involves a coordinate transformation from the two-dimensional space of CT scanning to the three-dimensional space of stereotactic surgery.

Although there has been a wide range of methods and devices designed to implement such a coordinate conversion, most of the devices have had a similar conceptual approach, wherein the resulting devices have left stereotactic surgery as being perceived as an esoteric, cumbersome, expensive, and time consuming procedure.

These prior art devices and methods typically utilize a frame mounted to the patient's skull by four pins or screws. Such devices have been found to be quite accurate and reliable and have allowed targets within a skull to be accessed with an accuracy of 1 mm. or less. They have allowed small, relatively inaccessible tumors to be biopsied with minor morbidity and practically absent mortality. These devices have also given surgeons a means of biopsying accessible tumors that are radiosensitive without the need for a formal craniotomy, a procedure that carries a much higher mortality and morbidity than stereotactic surgical procedures. In addition, such devices have provided a means for implementing new modalities for treating hematomas and abscesses, as well as the placement of radioisotopes and chemotherapeutic agents in the treatment of malignant brain tumors.

Despite these advances, there are characteristics of current stereotactic instruments which have severely limited their potential widespread application. The performance of careful stereotactic procedures on a regular basis with the prior art systems available requires much operating room time to be wasted during the procedure. Processing of X-ray pictures, target point calculations, and cumbersome mechanical adjustments on stereotactic frames add time to the operation. The inability of these systems to be reused on the same patient without recalculating target points also adds to their inefficiency. Although the prior art stereotactic instruments are adequate for reaching a single intracranial target point, rapid access to multiple targets during a procedure is inconvenient. Furthermore, the prior art devices are extremely expensive and are quite complicated to employ, thereby making their appeal to the surgeon in private practice quite limited. Some of the prior art systems require modifications of existing CT scanning software, or alternatively, require software generated coordinates determined from a hand-held calculator as part of the system. The frame required by these prior art devices requires fixation to the skull of the patient, typically via four screws, whereby the frame is quite cumbersome and uncomfortable. Additionally, the frame cannot be left on the patient's head if the same procedure is to be repeated at a later date. If subsequent stereotactic procedures are to be performed, the frame must be reapplied at the time of the second procedure, including the step of again using a CT scanner to calculate the coordinates of the target point within the skull.

Accordingly, prior to the development of the present method and apparatus for performing stereotactic surgery, there has been no method and apparatus for performing stereotactic surgery which: is compact, inexpensive, easy to use, precise, and comfortable; permits reaccessing of a target within the skull without additional CT scanning and coordinate recalculation; and does not require a bulky skull mounted frame. Therefore, the art has sought a method and an apparatus for performing stereotactic surgery which: does not require a skull mounted frame; is compact, inexpensive, easy to use, precise and comfortable; and permits reaccessing a target within the skull without re-scanning and coordinate recalculation.

SUMMARY OF THE INVENTION

In accordance with the invention, the foregoing advantages have been achieved through the present method and apparatus for performing stereotactic surgery. The method for performing stereotactic surgery, in accordance with the present invention, includes the steps of: establishing a first, pre-determined geometric relationship between a positioning fixture attached to both the skull and to a support surface upon which the skull is disposed; scanning the skull to produce an image of the target within the skull with respect to the positioning fixture; transferring at least a portion of the positioning fixture to a phantom fixture and disposing the positioning fixture portion with respect to the phantom fixture to establish a second, predetermined geometric relationship therebetween, which is identical to the first, predetermined geometric relationship, whereby the slope of the skull where the positioning fixture is attached to the skull is duplicated within the phantom fixture; disposing a phantom target within the phantom fixture at a location which corresponds to the location of the target within the skull; determining the trajectory and distance of a medical instrument extending from the positioning fixture portion to the phantom target; attaching the portion of the positioning fixture to the skull in the same location it was originally attached to the skull; and inserting the medical instrument through the positioning fixture in the trajectory determined from the phantom fixture, whereby the medical instrument will intersect the target in the skull.

Another feature of the present invention is that the positioning fixture may be attached to the support surface by an attachment member having first and second end portions and the first predetermined geometric relationship is the attachment member disposed coplanar with the support surface; and the second, predetermined geometric relationship is the attachment member disposed coplanar with the phantom fixture. A further feature of the present invention includes the steps of: moveably associating the first end portion of the attachment member with respect to the positioning fixture; and securing the attachment member with respect to the positioning fixture prior to scanning the skull.

A further feature of the present invention may include the steps of: moveably associating the attachment member with respect to at least a portion of the positioning fixture by using a first positioning ball secured to the first end portion of the attachment member; and the first positioning ball may be rotatably received within the positioning fixture.

Another feature of the present invention may include the steps of: using an outer and inner gimbal in the phantom fixture; and disposing the positioning fixture portion within the inner gimbal in the second, predetermined geometric relationship. A further feature of the present invention is that the positioning fixture may be attached to the support surface by an attachment member having first and second end portions; the first, predetermined geometric relationship is the attachment member disposed coplanar with the support surface; the second geometric relationship is the attachment member orthogonally disposed with respect to the phantom fixture; and while the positioning fixture portion is fixed with respect to the attachment member, the outer and inner gimbals are adjusted to receive the positioning fixture portion.

In accordance with the invention, the foregoing advantages have been achieved through the present system for performing stereotactic surgery. The system for performing stereotactic surgery, in accordance with the present invention, may include: a positioning fixture having associated therewith, a means for attaching the positioning fixture to both the skull and to a support surface upon which the skull is disposed; the positioning fixture including means for establishing a first, predetermined geometric relationship between the positioning fixture and the support surface; and a phantom fixture, which may include: means for receiving at least a portion of the positioning fixture; means for establishing a second, predetermined geometric relationship between the positioning fixture portion and the phantom fixture, wherein the second geometric relationship is identical to the first geometric relationship, whereby the slope of the skull where the positioning fixture is attached to the skull may be duplicated within the phantom fixture.

Another feature of the system in accordance with the present invention is that the means for attaching the positioning fixture may include an attachment member having first and second end portions; in the first, predetermined geometric relationship, the attachment member is disposed coplanar with the support surface; and in the second, predetermined geometric relationship, the attachment member is disposed coplanar with the phantom fixture.

An additional feature of the system of the present invention is that the means for establishing the first, predetermined geometric relationship, may include the first end portion of the attachment member being moveably associated with respect to the positioning fixture; and the positioning fixture may include means for locking the attachment member with respect to at least a portion of the positioning fixture. A further feature of the system of the present invention is that the means for establishing the second, predetermined geometric relationship, may include an inner and outer gimbal associated with the phantom fixture; the means for receiving at least a portion of the positioning fixture being associated with the inner gimbal.

The method and apparatus for performing stereotactic surgery of the present invention, when compared with previously proposed prior art methods and apparatus, have the advantages of being: compact, inexpensive, easy to use, precise, and comfortable for the patient; does not require a skull mounted frame; and permits reaccessing target areas within the skull without recalculating coordinates or rescanning the skull.

While the invention will be described in connection with the preferred embodiment, it will be understood that it is not intended to limit the invention to that embodiment. On the contrary, it is intended to cover all alternatives, modifications, and equivalents as may be included within the spirit and scope of the invention as defined by the appended claims.

DETAILED DESCRIPTION OF THE INVENTION

Figure 1:
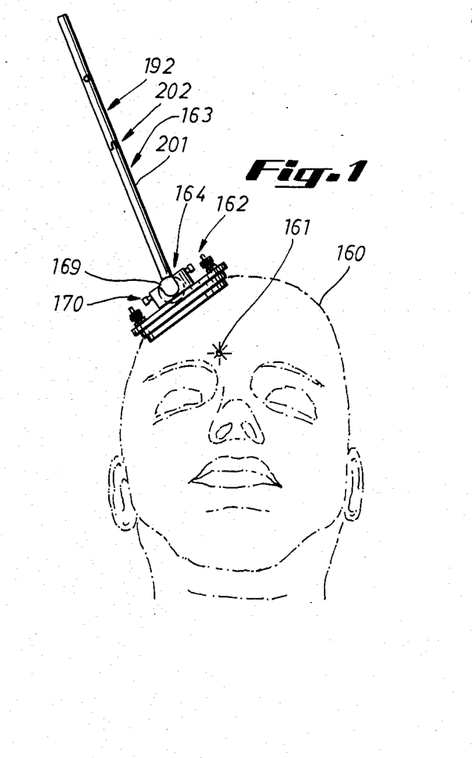
FIG. 1 is a front view of a patient (shown in dotted lines) with the positioning fixture of the present invention disposed upon the patient's skull.
Figure 2:
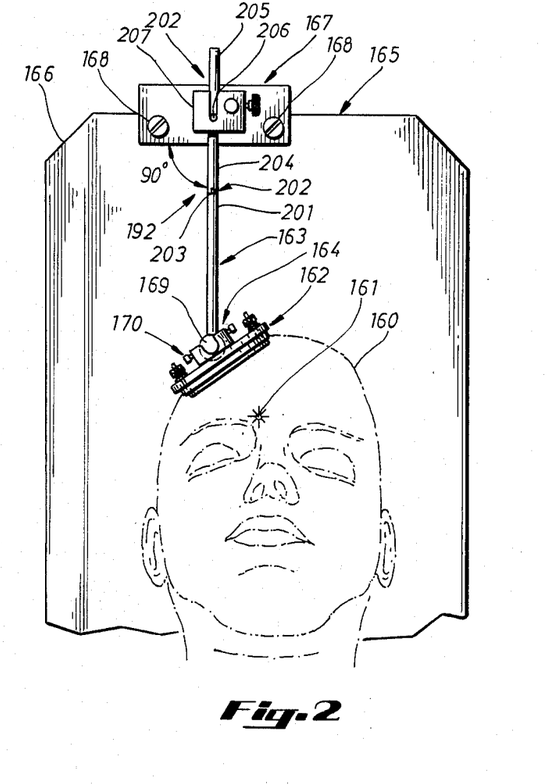
FIG. 2 is a top view of a patient (shown in dotted lines) being disposed upon a support surface, with the positioning fixture of the present invention disposed on the patient's skull.
Figure 3:
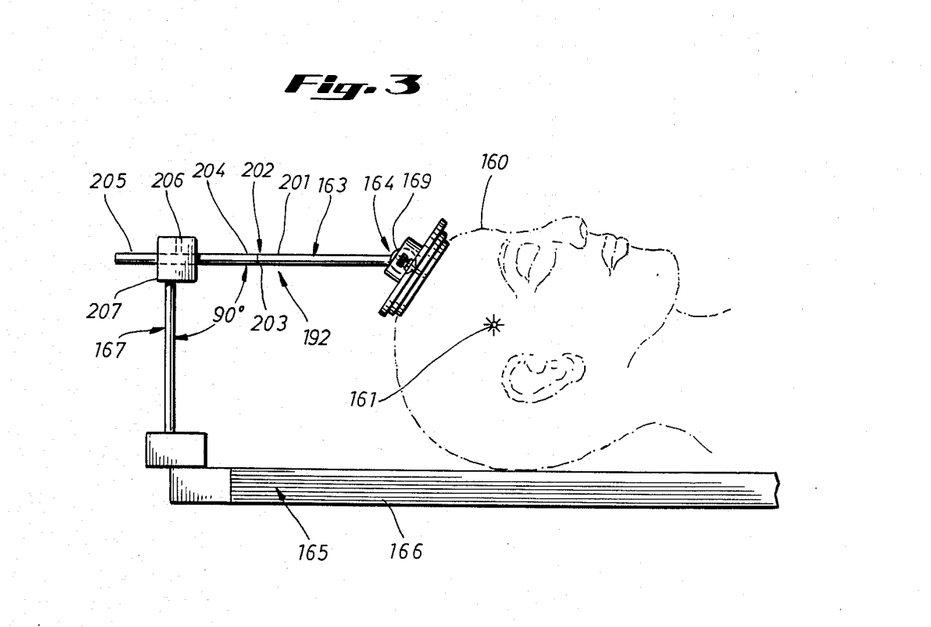
FIG. 3 is a side view of a patient (shown in dotted lines) disposed upon a support surface with the positioning fixture of the present invention disposed on the patient's skull.

With respect to FIGS. 1-6, the method for performing stereotactic surgery with a medical instrument upon a target within a skull will be generally described. Throughout FIGS. 1-6, the patient's skull 160 is shown in dotted lines, and target 161 is illustrated to represent the abnormality which is desired to be treated. For example, target 161 could be a hematoma, abscess or tumor. With reference to FIG. 1, a positioning fixture 162 is attached to skull 160 in a manner to be hereinafter described in greater detail. Preferably, positioning fixture 162 is constructed in accordance with the present invention, as will be hereinafter described in greater detail. The location at which positioning fixture 162 is attached to skull 160 may be determined by the location of target 161 within skull 160, as well as by a trial fit of positioning fixture 162 to skull 160. As seen in FIGS. 1-3, positioning fixture 162 may have an attachment member 163 associated therewith. Attachment member 163 has a first end portion 164 moveably associated with respect to positioning fixture 162, as will be hereinafter described in greater detail.

With reference to FIGS. 2 and 3, the patient is laid upon a support surface 165 and skull 160 is thus disposed upon support surface 165. Typically, support surface 165 is a conventional, planar imaging table 166 which is used in connection with a conventional scanning device, such as a CT scanner. As seen in FIGS. 2 and 3, attachment member 163 is moved with respect to positioning fixture 162, so that attachment member 163 may mate with an upright bracket 167 which is secured to imaging table 166 in any suitable fashion, such as by a clamp or screws 168. With the positioning fixture 162 and attachment member 163 in the positions illustrated in FIGS. 2 and 3, a first, predetermined geometric relationship has been established between the positioning fixture 162 and the support surface 165 upon which skull 160 is disposed. Preferably, this first, pre- determined geometric relationship is with attachment member 163 being disposed coplanar with support surface 165. By use of the term "coplanar" it is meant that the longitudinal axis of attachment member 163 is caused to lie in a plane which is parallel with the longitudinal axis of the support surface 165, as seen in FIG. 3, and in a plane which is perpendicular to the longitudinal axis of support surface 165, as seen in FIG. 2.

Figure 4:
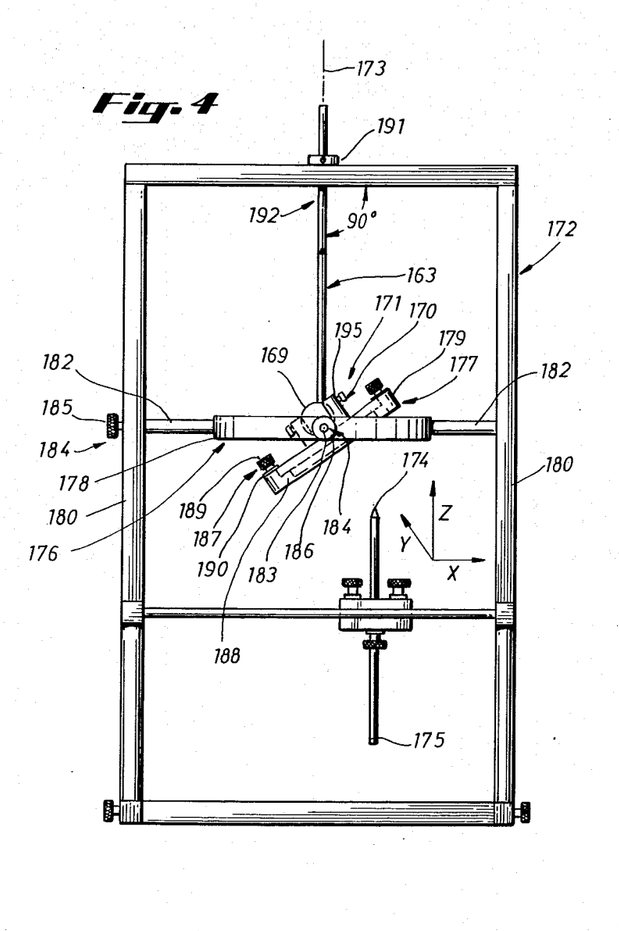
FIG. 4 is a front view of a phantom fixture in accordance with the present invention.

With the patient's skull 160 disposed upon support surface 165, as shown in FIGS. 2 and 3, and the attachment member disposed in the first, predetermined geometric relationship with respect to support surface 165 and attached therebetween, the skull is then scanned by any suitable scanning device, such as a CT scanner, in a conventional manner. A radiopaque marker (not shown) is disposed in the center of the positioning fixture 162, whereby the scanning procedure produces a series of images of the target 161 with respect to the positioning fixture 162. After the scanning of skull 160 has been performed, at least a portion 171 of the positioning fixture 162 may be removed from the patient's skull 160 and transferred to a phantom fixture 172, as shown in FIG. 4. In this regard, preferably only a portion 171 of positioning fixture 162 is removed from skull 160; however, it is possible that the entire positioning fixture 162 could be removed from the patient's skull 160. Further, it should be noted that in contrast to the prior art methods and devices previously described, if a portion of positioning fixture 162 remains on skull 160, such positioning fixture portion is much more compact with respect to the patient's skull 160, as well as being much more comfortable for the patient.

Further, with regard to FIGS. 1-3, it is seen that the first end portion 164 of attachment member 163 may be moveably associated with respect to positioning fixture 162, as by securing the first end portion 164 of attachment member 163 to a positioning ball 169, and positioning ball 169 is rotatably received within the positioning fixture 162. Accordingly, attachment member 163 may be freely moved with respect to positioning fixture 162, whereby attachment member 163 can be disposed in the geometric relationship shown in FIGS. 2 and 3. Positioning fixture 162 may also be provided with a means for securing, or locking, 170 the attachment member 163 with respect to positioning fixture 162. Prior to scanning the skull 160, when attachment member 163 and positioning fixture 162 are disposed in the geometric relationship shown in FIGS. 2 and 3, positioning ball locking means 170, to be hereinafter described in greater detail, is preferably engaged, whereby skull 160, attachment member 163 and positioning fixture 162 will remain disposed in the geometric relationship shown in FIGS. 2 and 3 throughout the scanning procedure. After the scanning procedure has been performed, the portion 171 of positioning fixture 162 is transferred to phantom fixture 172. Preferably, positioning fixture portion 171 includes attachment member 163, positioning ball 169, and positioning ball locking means 170, as shown in FIG. 4, and as will be hereinafter described in greater detail.

With reference to FIG. 4, the positioning fixture portion 171, including attachment member 163 and positioning ball 169, which remains in the locked position shown in FIGS. 2 and 3, has been transferred to phantom fixture 172, and is disposed with respect to phantom fixture 172 in a second, predetermined geometric relationship therebetween. The second, predetermined geometric relationship is shown as being attachment member 163 being disposed coplanar with phantom fixture 172. In this regard, the term "coplanar" is defined as meaning that the attachment member 163 lies in planes which are all parallel with respect to the longitudinal axis 173 (as shown in dotted lines in FIGS. 4 and 13), of the phantom fixture 172. Thus, the second, predetermined geometric relationship between positioning fixture portion 171 and phantom fixture 172 is identical to the first, predetermined geometric relationship between positioning fixture 162 and support surface 165. Since the positioning fixture portion 171 disposed within phantom fixture 172 was originally disposed upon skull 160, the slope of skull 160 at the location where positioning fixture 162 was attached to skull 160 has been duplicated within phantom fixture 172. In summary, with the attachment member 163, including positioning fixture portion 171 secured thereto, disposed within phantom fixture 172 in the same position as shown in FIGS. 2 and 3, the second geometric relationship between the attachment member 163 and the phantom fixture 172 is the same as the first geometric relationship between the attachment member and support surface 165. Since the disposition of attachment member 163 with respect to the positioning fixture portion 171 is identical in FIGS. 2 and 3, and FIG. 4, and since positioning ball 169 has been locked with respect to positioning fixture 162, the slope of the skull 160 where the positioning fixture 162 has been attached to skull 160 is duplicated within the phantom fixture 172.

Still with reference to FIG. 4, a phantom target 174 is disposed within the phantom fixture 172 at a location which corresponds to the location of the target 161 within skull 160. The three-dimensional spatial coordinates of phantom target 174, representative of target 161 within skull 160, are determined in a conventional manner from the scanning procedure. The x and y coordinates of the target 161 within skull 160 may be read from the generated images from the scanning procedure and the z coordinate may be obtained by noting the difference in imaging table 166 displacement between the image slice containing the positioning fixture 162 and the image slice containing the target 161, insofar as the series of generated images disclose the target with respect to positioning fixture 162. In this regard, a radiopaque marker (not shown) is preferably disposed at the center of positioning ball 169, and, as will hereinafter be described in greater detail, the positioning fixture 162, including positioning ball 169 are made of a radiolucent material, such as LEXAN ®, so as not to interfere with the images produced by the scanning procedure. Thus, the coordinates of the target 161 are generated in relation to the positioning fixture 162. They can then be transferred to the phantom fixture 172 in a conventional manner, so that phantom target 174, which is preferably the tip of a phantom target rod 175, may be disposed within phantom fixture 172 at a spatial location which corresponds to the location of the target 161 within skull 160. Target rod 175, and in turn phantom target 174, may be disposed anywhere within phantom fixture 172 in a conventional manner, as will hereinafter be described in greater detail in connection with FIG. 13.

Figure 13:
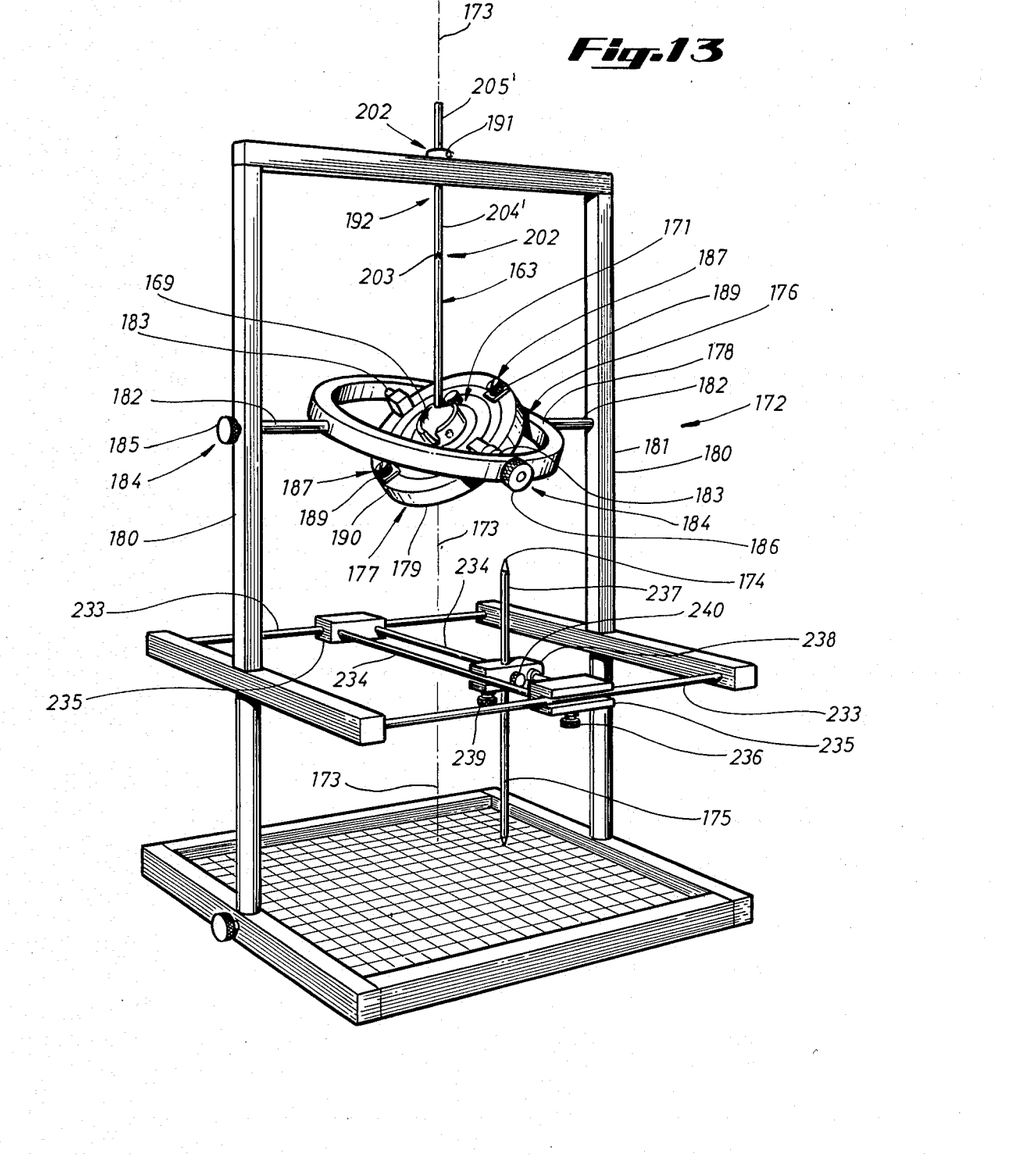
FIG. 13 is a perspective view of a phantom fixture of the present invention.

With reference to FIGS. 4 and 13, phantom fixture 172 preferably utilizes an outer and inner gimbal 176, 177. As seen in FIGS. 4 and 13, the positioning fixture portion 171 is disposed within the inner gimbal 177. Preferably, outer and inner gimbals 176, 177 are constructed as an outer gimbal ring 178 and an inner gimbal ring 179. Outer gimbal 176 may be preferably disposed between two upright frame members 180 which form a portion of a frame 181 of phantom fixture 172. Outer gimbal 176 may be rotated about an axis defined by two rod members 182 journaled within uprights 180. Likewise, inner gimbal 177 is mounted within outer gimbal 176 as to be freely rotatable with respect to outer gimbal 176, as by mounting inner gimbal 177 upon rod members 183 which are rotatably mounted in outer gimbal 176. Outer and inner gimbals 176, 177 may be rotated independently, the inner gimbal 177 rotating within outer gimbal 176. Thus, by adjusting the rotation of the outer and inner gimbals 176, 177 within phantom fixture 172, the inner gimbal 177 can be adjusted to receive the positioning fixture portion 171 when positioning fixture portion 171 is transferred, along with attachment member 163 in its locked position with respect to positioning fixture 171, and thus disposed within phantom fixture 172. Therefore, positioning fixture portion 171 will lie within inner gimbal 177 of phantom fixture 172, so as to be disposed in the second, predetermined geometric relationship previously described. It should of course be understood that the configuration of inner and outer gimbals 177, 176 could be any other configuration other than inner and outer gimbal rings 179, 178, so long as inner gimbal 177 is free to rotate within outer gimbal 176, and outer gimbal 176 can freely rotate within phantom fixture 172. For example, inner gimbal and outer gimbal 177, 176 could have a square configuration, wherein the inner square (not shown) is sized so as to be able to rotate within the outer square (not shown).

Still with reference to FIGS. 4 and 13, phantom fixture 172 may preferably include means for locking 184 the inner and outer gimbals 177, 176 with respect to phantom fixture 172. Preferably, locking means 184 for gimbals 176, 177 may be any suitable device which can lock rod member 182 with respect to uprights 180 of phantom fixture 172, and lock rod members 183 with respect to outer gimbal 176. For example, locking means 184 can comprise two thumb nuts 185, 186. Thumb nut 185 can engage upright 180, thus securing rod member 182, and in turn outer gimbal 176 in a fixed position. Thumb nut 186 can engage outer gimbal 176 which in turn locks the position of rod member 183 with respect to outer gimbal 178. Further, the inner gimbal 177 includes a means for locking 187 the positioning fixture portion 171 with respect to inner gimbal 177. In this regard, as seen in FIG. 4, inner gimbal 177 may be provided with an interior recessed flange member 188 upon which positioning fixture portion 171 rests upon when it is received within inner gimbal 177. Locking means 187, which preferably comprises at least one lock nut 189, and preferably two lock nuts 189, can be threaded downwardly to bear upon a small plate 190 which in turn bears against inner gimbal 177 and positioning fixture portion 171 as shown in FIG. 4. After positioning fixture portion 171, including attachment member 163, are disposed within phantom fixture 172, inner and outer gimbals, 177, 176 are adjusted as previously described. Locking means 184, 187 may then be engaged to lock inner and outer gimbals 177, 176 in the position shown in FIG. 4, and positioning fixture portion 171 is then secured within inner gimbal 177.

After the positioning fixture portion 171 and phantom target 174 have been disposed within phantom fixture 172 as previously described and as illustrated in FIG. 4, it is necessary to determine the trajectory and distance of a medical instrument extending from the positioning fixture portion 171 to the phantom target 174. This is accomplished by releasing positioning ball locking means 170, whereby positioning ball 169 and attachment member 163 may be removed from the phantom fixture 172, leaving the positioning fixture portion 171 disposed within inner gimbal 177 in the locked positions previously described. A suitable lock 191 associated with phantom fixture 172 and engageable with the second end portion 192 of attachment member 163 may be disengaged to permit the removal of attachment member 163 and in turn positioning ball 169 from phantom fixture 172.

Figure 5:
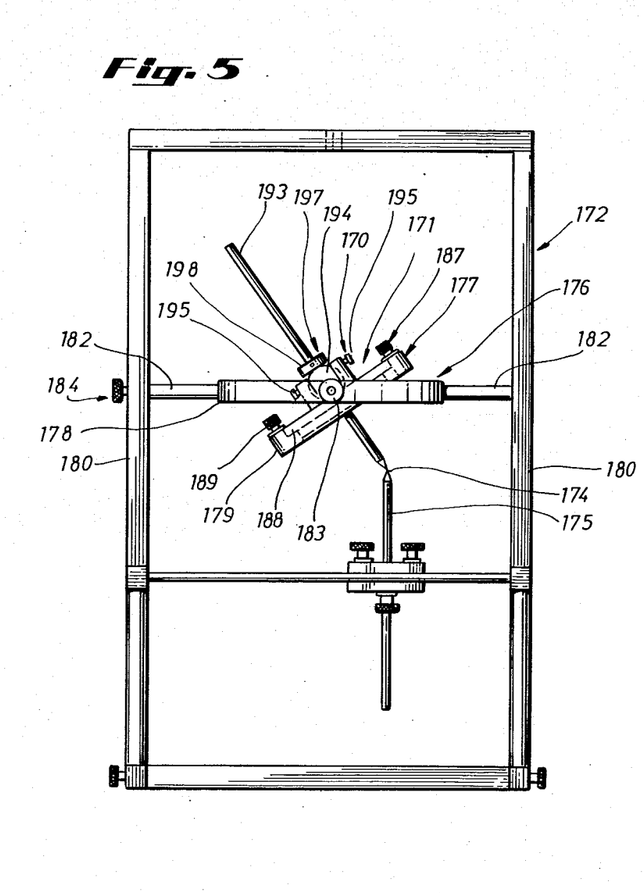
FIG. 5 is another front view of a phantom fixture in accordance with the present invention.

The trajectory and distance of a medical instrument extending from the positioning fixture portion 171 to the phantom target 174 is then determined by inserting a medical instrument 193 (FIG. 5) through the positioning fixture portion 171 until it intersects the phantom target 174. The medical instrument 193 may then be locked with respect to the positioning fixture portion 171 at the desired trajectory and distance to the phantom target 174. This step may be accomplished by associating a trajectory ball 194 with the positioning fixture portion 171; inserting the medical instrument 193 through the trajectory ball 194 and adjusting it until it intersects the phantom target 174 as shown in FIG. 5. Trajectory ball 194 may then be locked with respect to positioning fixture portion 171 as by engaging positioning ball locking means 170 with trajectory ball 194. For example, positioning ball locking means 170, which can also be used to lock trajectory ball 194, is preferably at least one, or more, locking screws 195 which securely engage trajectory ball 194 and fix its position with respect to positioning fixture portion 171. Trajectory ball 194 is preferably provided with a passageway 196 (FIGS. 14 and 15) extending therethrough which is adapted to permit the medical instrument 193 to pass through the trajectory ball 194. Medical instrument 193 may be a probe useful for obtaining a portion of a tumor for biopsy purposes, as well as a device which can be utilized to drain an abscess in the brain or to aspirate a cyst.

Figure 14:
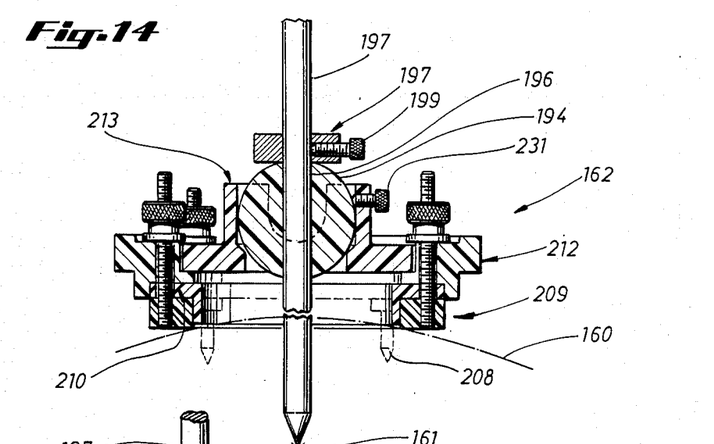
FIG. 14 is a partial cross-sectional view of a positioning fixture of the present invention, including a medical instrument disposed therein.
Figure 15:
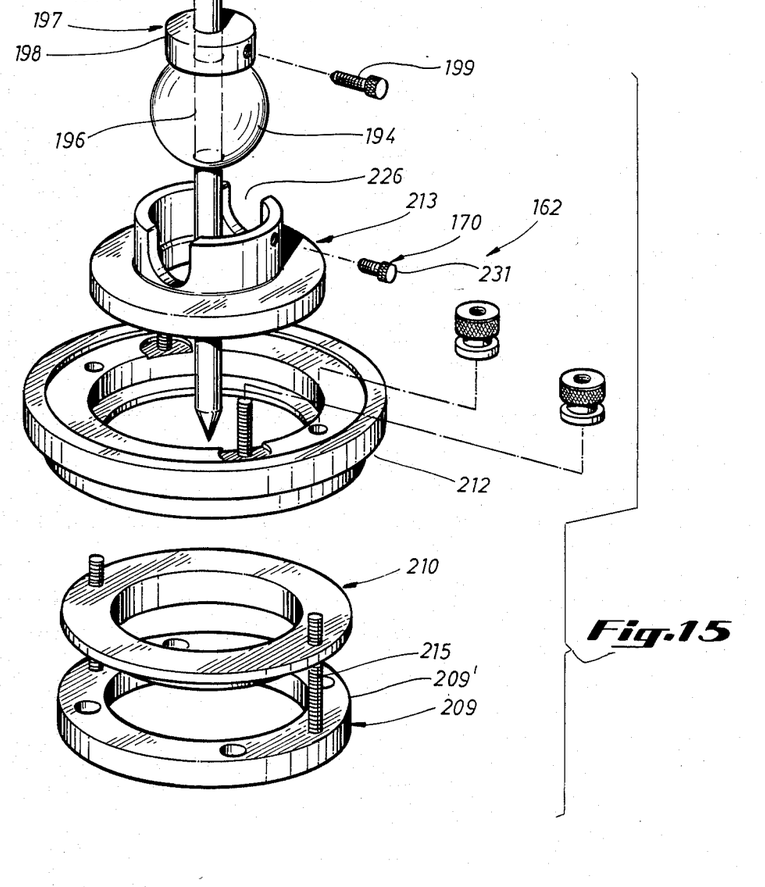
FIG. 15 is a perspective, exploded view of the positioning fixture of FIG. 14.

Still with reference to FIG. 5, after trajectory ball 194 has been locked with respect to positioning fixture portion 171, whereby medical instrument 193 has intersected phantom target 174, the distance from the positioning fixture portion 171 to the phantom target 174 is preferably indicated. The indication of this distance can be accomplished by associating the depth stop member 197 with the medical instrument 193 after trajectory ball 194 has been locked with respect to positioning fixture portion 171. Depth stop member 197 may be a ring 198 which is disposed about medical instrument 193 and includes set screw 199 (FIGS. 14 and 15). Upon engagement of set screw 199 into medical instrument 193, ring 198 prevents further inward movement of medical instrument 193 through trajectory ball 194.

Figure 6:
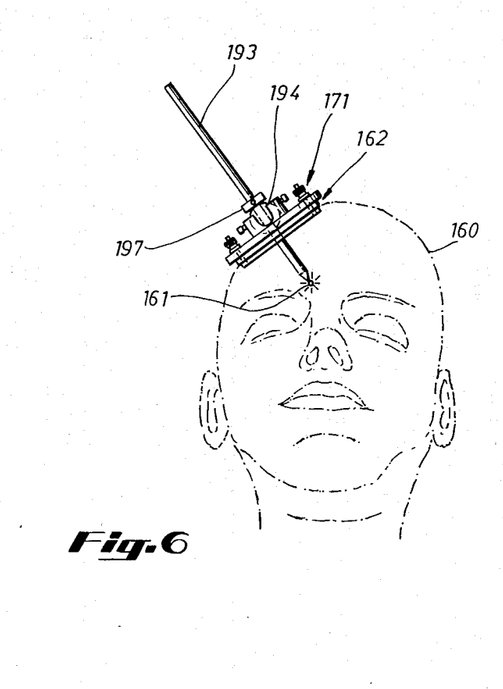
FIG. 6 is a front view of a patient (shown in dotted lines) with the positioning fixture of the present invention being used to direct a medical instrument toward a target within the patient's skull.

Upon completion of the step of determining the trajectory and distance of the medical instrument 193 to the phantom target 174, locking means 187 is released as by removing lock nuts 189. Positioning fixture portion 171, including medical instrument 193 and the locked trajectory ball 194 may then be removed from the phantom fixture. These components are then sterilized in a conventional manner. After sterilization, the positioning fixture portion 171 is attached upon skull 160, as shown in FIG. 6, in the same location it was originally attached to the skull 160 as shown in FIG. 1. While positioning fixture portion 171 is being reattached to skull 160, trajectory ball 194 remains firmly locked within position fixture portion 171, while medical instrument 193 with depth stop member 197 are kept sterile. It should be noted that prior to or after the attachment of positioning fixture portion 171 to skull 160, skull 160 has had a hole drilled therein in a conventional manner to allow subsequent insertion of medical instrument 193 into skull 160.

Still with reference to FIG. 6, after the positioning fixture portion 171 has been reattached to skull 160 and the requisite hole has been drilled in skull 160, medical instrument 193 is inserted through the positioning fixture 162 in the trajectory determined from the phantom fixture 172, as by trajectory ball 194. The medical instrument 193 is inserted until it intersects the target 161 within skull 160, as shown in FIG. 6. The desired medical treatment of target 161 may then be performed by medical instrument 193.

It should be noted that if instead of only a portion 171 of positioning fixture 162 being utilized within phantom fixture 172, as previously described, the entire positioning fixture 162 could be removed from skull 160 after the first, predetermined geometric relationship was established, as described in connection with FIGS. 2 and 3. The entire positioning fixture 162 would be reattached to skull 160 in the same location it was originally attached to the skull 160 as shown in FIG. 1, prior to insertion of medical instrument 193. It should further be noted that once the trajectory and distance of the medical instrument from the positioning fixture 162 to the target 161 has been determined in the manner previously described, it is possible to store the positioning fixture 162, or positioning fixture portion 171, with the trajectory ball 194 firmly locked in place within positioning fixture 162, along with storing medical instrument 193 with depth stop member 197 firmly engaged therewith. Thus the patient can return at a subsequent date to have the stereotactic surgery performed upon target 161. All that is required is to insure that positioning fixture 162 is reattached to skull 160 at the later time in precisely the same location it was originally attached to the skull 160 as shown in FIG. 1. In this regard, positioning fixture 162, or a portion of a positioning fixture 162, can be secured to skull 160 in a conventional manner by the use of at least one and preferably two or more self-tapping titanium screws. Upon removal of such screws, the positioning fixture 162 can be removed from skull 160 and it can be reattached to the identical site upon skull 160 by utilizing the same positioning fixture 162 at a later date, and securing it to skull 160 with screws engaging the previously formed holes in skull 160. Additionally, a patient's positioning fixture 162 with his trajectory ball 194 firmly locked therein may be stored; and either the medical instrument 193 with depth stop member 197 firmly locked thereon may be stored, or, alternatively, a record of the distance from the depth stop member to either end of the medical instrument 193 may be retained. Thus, a patient can return for subsequent stereotactic surgery treatments on the same target 161, without the necessity of rescanning the patient's skull 160 and performing the steps utilizing the phantom fixture.

In practicing the foregoing described method, it is preferred to utilize an elongate rod 201 (FIGS. 1-3) for attachment member 163, and to include a means for identically orientating 202 the second end portion 192 of attachment member 163 with respect to both the support surface 165 and the phantom fixture 172. With reference to FIGS. 2, 3, and 13, a mating tongue and groove connection can be used as the means for identically orientating 202 the second end portion 192 of the attachment member 163. Preferably the mating tongue and groove connection 203 is associated with the second end 192 of attachment member 163 and an end 204 of an elongate rod 205 disposed coplanar with respect to the support surface 165 (FIGS. 2 and 3) and an end 204' of an elongate rod 205' disposed coplanar with respect to the phantom fixture 172, as shown in FIG. 13. Accordingly, after scanning of a patient, at least a portion 171 of positioning fixture 162 is removed from the skull 160, including attachment member 163 being secured in a fixed relationship with respect to the positioning fixture portion 171, as previously described. If it is then disposed within phantom fixture 172 as previously described, the means for orientating 202, or mating tongue and groove connection 203, will insure that the positioning fixture portion 171 is precisely and accurately orientated with respect to both the support surface 165 and the phantom fixture 172. Alternatively, the means for orientating 202 attachment member 163 with respect to both the support surface 165 and the phantom fixture 172 can comprise utilizing a single elongate rod without a mating tongue and groove connection 203, and using a means for orientating 202 comprised of a pin 206 which is engageable with a slotted support member 207 disposed on bracket 167 as shown in FIGS. 2 and 3. Likewise, phantom fixture 172 would be provided with the same type of slotted bracket 207 in lieu of lock member 191 (FIG. 13), whereby attachment member 163 will be accurately orientated with respect to both the support surface 165 and the phantom fixture 172.

Turning now to FIGS. 9-12, a positioning fixture 162 which comprises a portion of a system for performing stereotactic surgery, and which positioning fixture 162 may be utilized in connection with the method for performing stereotactic surgery previously described, will be set forth. Positioning fixture 162 which is adapted to be attached to skull 160 by at least one, and preferably two or more self-tapping screws 208, preferably comprises: a primary, or skull, plate member 209; guide plate member 210; cover plate member 211; secondary plate member 212; ball socket member 213; and attachment member 163. Primary, or skull plate member 209 is preferably an annular ring provided with at least one, and preferably two or more holes 214 through which screws 208 pass to engage skull 160. Skull plate member 209 is additionally provided with at least two alignment studs 215 which serve to accurately align guide plate member 210, cover plate member 211 and secondary plate member 212 with respect to the skull plate member 209, insofar as each of those components is provided with two openings 216 which mate with alignment studs 215 when those components are placed over skull plate member 209 and alignment studs 215. Guide plate member 210 is a generally annular member 217 having a downwardly depending annular flange member 218, and guide plate member overlies skull plate member 209 with the depending flange 218 being disposed within skull plate member 209. Cover plate member 211 is a flat disk which seals off the exposed portion of skull 160 lying beneath the opening defined by guide plate member 210 and skull plate member 209 when the secondary plate member 212 is not associated with skull plate member 209, as will be hereinafter described in greater detail. Of course, when it is desired to perform stereotactic surgery upon skull 160, in accordance with a method such as that previously described, cover plate member 211 would not be utilized in conjunction with positioning fixture 162.

Figure 9:
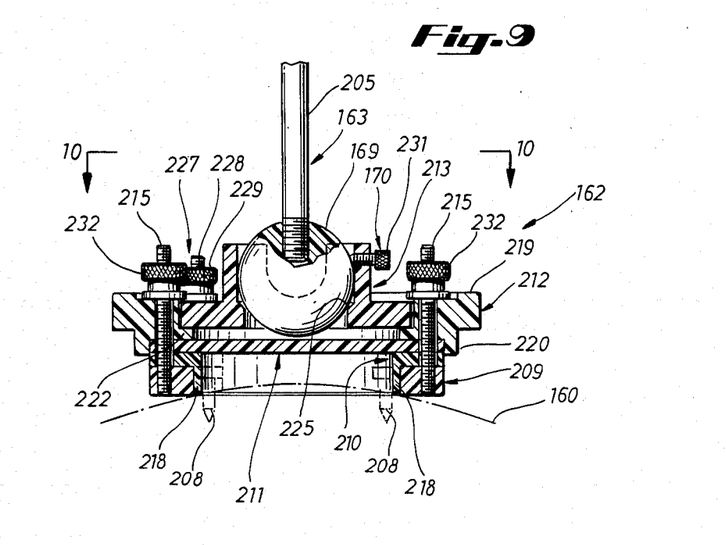
FIG. 9 is a partial cross-sectional view of the positioning fixture taken along line 9—9 of FIG. 10.
Figure 10:
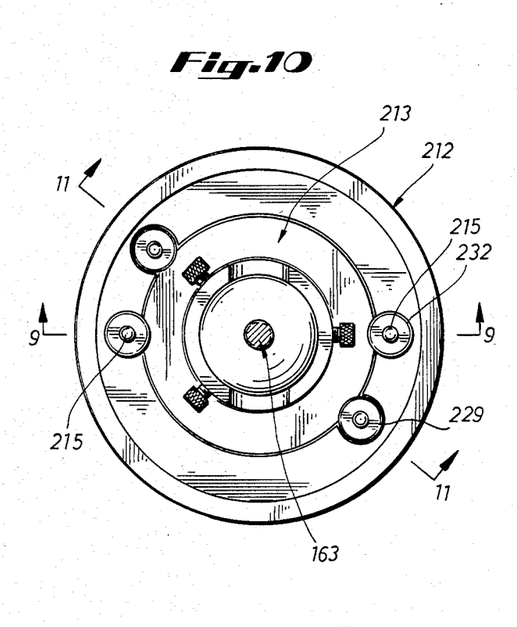
FIG. 10 is a partial cross-sectional view of the positioning fixture taken along line 10—10 of FIG. 9.
Figure 11:
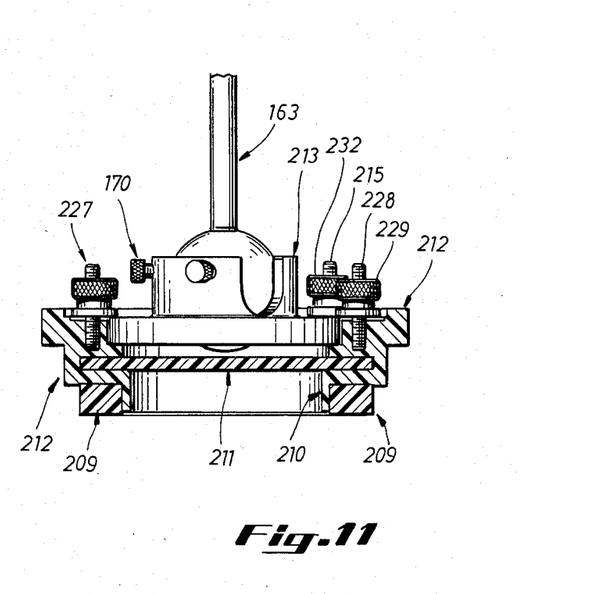
FIG. 11 is a partial cross-sectional view of the positioning fixture of the present invention taken along line 11—11 of FIG. 10.
Figure 12:
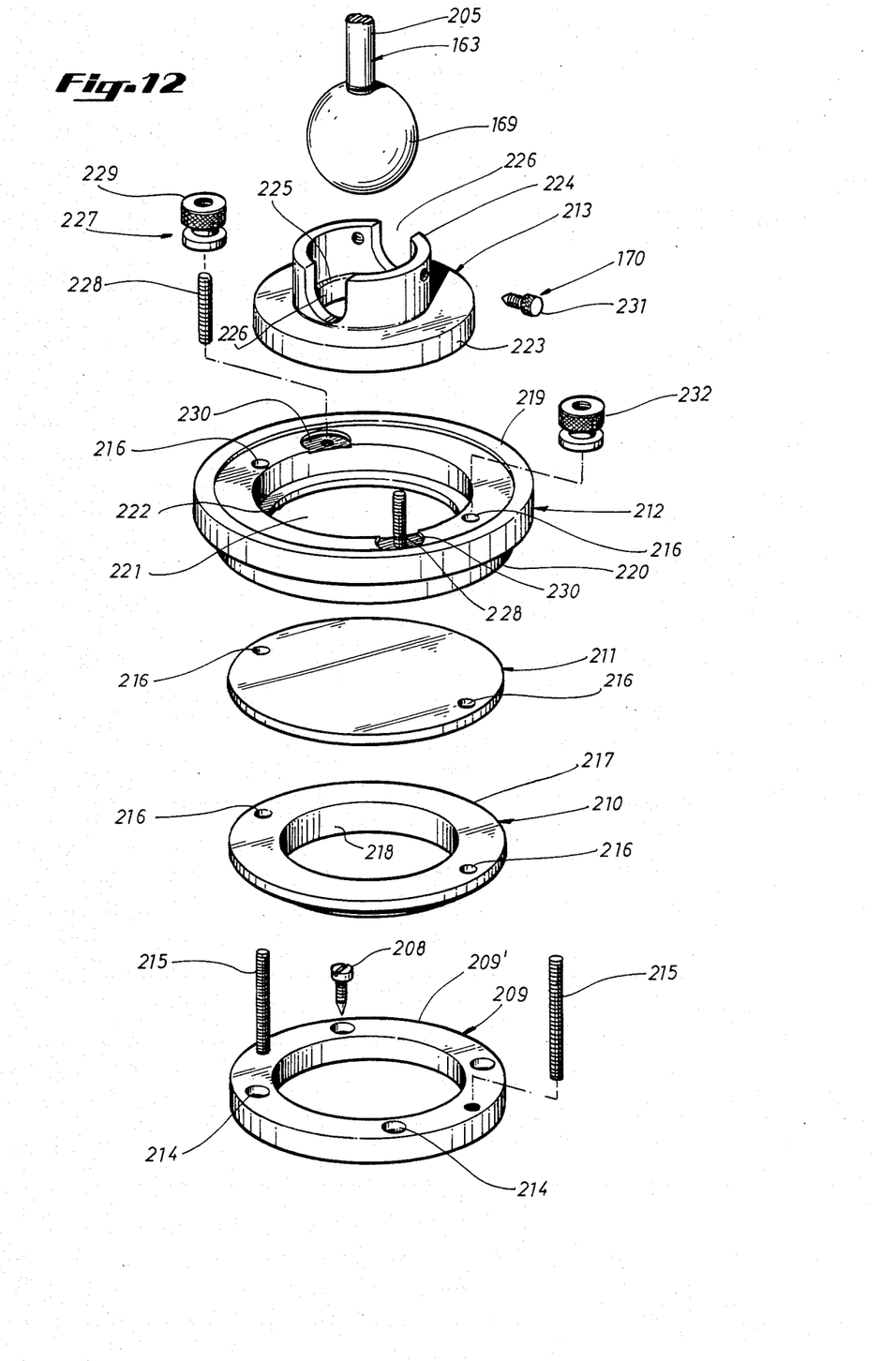
FIG. 12 is a perspective, exploded view of the positioning fixture of the present invention shown in FIGS. 9–11.

Still with reference to FIGS. 9-12, secondary plate member 212 is a generally annular shaped member 219, which upon being passed over alignment studs 215 overlies skull plate member 209. Secondary plate member 212 may include a lower downwardly depending flange member 220 which closely conforms to the outer configuration of cover plate member 211 and guide plate member 210. Secondary plate member 212 is also provided with an interior annular opening 221 which has an inwardly extending annular flange member 222, within which opening 221 the ball socket member 213 may be received, and the downward movement of the ball socket member 213 is restrained by the internal annular flange member 222. Ball socket member 213 may preferably comprise an annular disk member 223 having an upwardly extending cup-like flange 224 which is adapted to receive the attachment member 163. Ball socket member 213 may be provided with a slightly bevelled internal surface 225 (FIGS. 9 and 12) upon which positioning ball 169 of attachment member 163 rests. As seen in FIG. 9, attachment member 163 may be an elongate rod 205 threadably received within positioning ball 169.

The upwardly extending cup-like flange 224 of ball socket member 213 may have one or more sections removed therefrom, as shown at 226, to permit greater flexibility of movement of attachment member 163, or rod 205, in that positioning ball 169 could be rotated until rod 205 is disposed within area 226. Secondary plate member 212 is preferably provided with a means for locking 228 the ball socket member 213 with respect to the secondary plate member 212. Preferably, the locking means 227 comprises at least one, and preferably two upstanding threaded posts 228 and mating lock nuts which are capable of bearing down upon the annular disk member 223 of ball socket member 213 as illustrated in FIG. 9. In this regard, secondary plate member 212 may be slightly spot-faced adjacent threaded posts 228, as shown at 230 to enable lock nuts 229 to contact annular disk member 223 of ball socket member 213, when ball socket member 213 is disposed within secondary plate member 212. As previously described, a means for locking 170 positioning ball 169 with respect to positioning fixture 162 may be provided, as by disposing at least one or more threaded screws 231 which pass through the upwardly extending cup-like flange 224 of ball socket member 213 to engage positioning ball 169. Mating lock nuts 232 may be provided for alignment studs 215, whereby, as shown in FIG. 9, secondary plate member 212, cover plate member 211, and guide plate member 210 may be firmly secured to skull 160, upon tightening of lock nuts 232. Lock nuts 232 will also serve to restrain outward movement of ball socket member 213 from positioning fixture 162; however, ball socket member 213 would be free to rotate within annular opening 221 unless lock nuts 229 were tightened to engage the upper surface of annular disk member 223 of ball socket member 213.

When utilizing the positioning fixture 162 as shown in FIGS. 9-12 to practice the method for performing stereotactic surgery previously described, positioning fixture 162 would initially be disposed as illustrated in FIG. 9 upon skull 160, with ball socket member 213 freely rotatable with respect to secondary plate member 212, and attachment member 163 would likewise be free to rotate with respect to ball socket member 213. Upon establishing the first, predetermined geometric relationship illustrated and described in connection with FIGS. 2 and 3, locking means 227 for ball socket member 213 would be secured, as well as engaging locking means 170 with positioning ball 169. After the scanning procedure has been conducted, as previously described, a portion of the positioning fixture 162 is then transferred to the phantom fixture 172 as previously described. When utilizing the positioning fixture of 162 as illustrated in FIGS. 9-12, lock nuts 232 are removed and the secondary plate member 212, with the ball socket member 213 firmly locked therein, and with positioning ball 169 firmly locked within ball socket member 213, is removed from the skull 160. Lock nuts 232 may then be threaded upon alignment studs 212 to secure the cover plate member 211 and guide plate member 210 to the skull plate member 212 which remains firmly affixed to the skull. Thus, as previously described in connection with FIG. 4, the secondary plate member 212, ball socket member 213 and attachment member 163, or positioning ball 169 and rod 205 may be disposed within the phantom fixture 172 in the manner previously described.

FIGS. 14 and 15 illustrate the positioning fixture 162 when a trajectory ball 194 has been substituted for the positioning ball 169, with the trajectory and distance of the medical instrument 197 to the target having been determined as previously described. In this regard, FIG. 14 illustrates the insertion of the medical instrument 197 through positioning fixture 162 via trajectory ball 194 and its passageway 196, until medical instrument 197 intersects target 161 disposed within skull 160. Of course, cover plate member 211 is not utilized in conjunction with positioning fixture 162 when medical instrument 197 is being inserted through positioning fixture 162.

The components of positioning fixture 162 may be made of any suitable material having the requisite strength characteristics and ability to maintain close tolerances upon exposure to a source of heat necessary to sterilize the components. Preferably, skull plate member 209, guide plate member 210, cover plate member 211, secondary plate member 212, ball socket member 213, positioning ball 169 and trajectory ball 194 are all manufactured of LEXAN ®.

With reference to FIG. 13, additional features of a phantom fixture 172, which forms a part of the system for performing stereotactic surgery, and is useful in the practicing of the method for performing stereotactic surgery previously described, are shown. Phantom fixture 172 preferably includes two pair of guide rods 233, 234, disposed perpendicular to each other. Guide rods 234 are slideably mounted upon guide rods 233, as by mounting blocks 235. At least one guide block 235 is provided with a locking means 236 which permits the fixing of the x-coordinate for phantom target rod 237. Phantom target rod 237 is associated with a slideable mounting block 238 which is slideable along guide rod 234. Mounting block 238 has a locking means 239 which permits locking the phantom target rod 237 in the desired y-coordinate. Phantom target rod 237 is in turn vertically slideable within mounting block 238 whereby the z-coordinate of phantom target 174 can be established by engaging a locking means 240 which engages phantom target rod 237.

Figure 7:
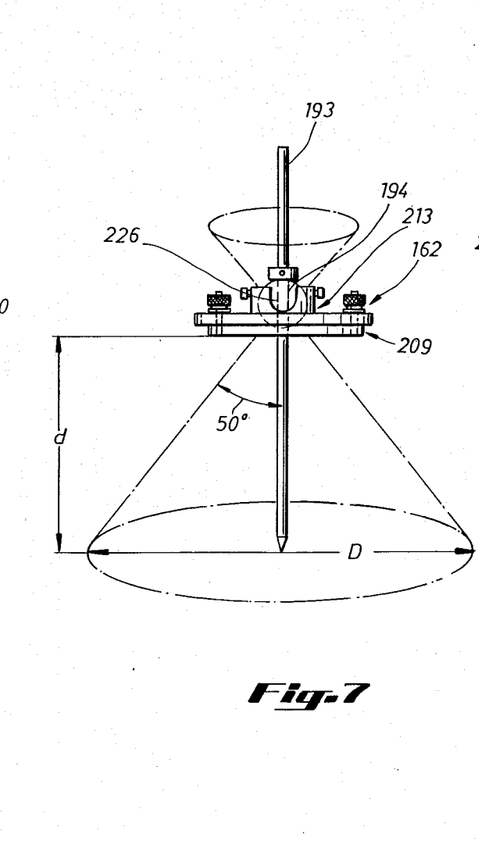
FIG. 7 is a front view of a positioning fixture in accordance with the present invention, illustrating the intracranial area accessibility of a positioning fixture of the present invention.

With reference to FIG. 7, a positioning fixture 162 in accordance with the present invention is shown having a medical instrument 193 inserted therethrough via a trajectory ball 194 disposed within ball socket member 213 and skull plate member 209. Due to the rotatability of the ball socket member 213 with respect to the skull plate member 209, as well as the open areas 226 formed in ball socket member 213, positioning fixture 162 allows full access to a diameter (D) slice of brain at a depth (d), wherein the diameter can be as large as 14 cm. and the depth can be up to 6 cm. Thus, multiple targets within the skull 160 can be intersected by medical instrument 193 from a single attachment of positioning fixture 162 to skull 160. Additionally, it should be noted that trajectory balls 194 could be utilized having multiple parallel passageways 196 disposed therein, whereby more than one medical instrument can intersect a potential target within the skull 160.

Figure 8:
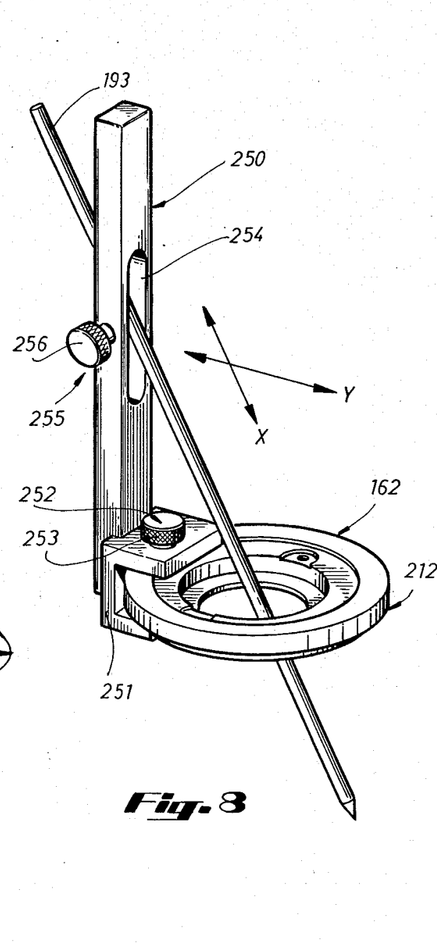
FIG. 8 is a perspective view of a stanchion clamp accessory for use with the present invention.

With reference to FIG. 8, an accessory stanchion clamp 250 is illustrated. Stanchion clamp 250 has at its lower end, a bracket 251 which is adapted to engage the secondary plate member 212 which has been affixed to the skull (not shown) as previously described. Bracket 251 may include a locking means 252, or threaded locking screw 253 which engages the upper surface of secondary plate member 212. The stanchion clamp 250 may further include a slot 254 through which a medical instrument 193 may pass, and a medical instrument locking means 255 or threaded locking screw 256, is provided to lock the medical instrument 193 with respect to the stanchion clamp 250. Stanchion clamp 250 can be utilized to perform stereotactically guided craniotomies through an opening as large as 3 cm. in diameter, as well as allows for the use of endoscopes, lasers, and ultrasound devices within the skull. After the trajectory and distance of medical instrument 193 to the target have been determined in the manner previously described, the positioning fixture portion 171 with trajectory ball 194 therein is secured to skull plate member 209. Stanchion clamp member 250 is then attached to the secondary plate member 212, whereby medical instrument 193 may pass through the trajectory ball (not shown). Upon removal of the ball socket member 213, including the trajectory ball 194, positioning fixture 162 with stanchion clamp 250 would appear as illustrated in FIG. 8, whereby greater access is allowed to the interior of the skull. Additionally, stanchion clamp 250 supports lineal movement of the medical instrument 193 along the x and y axes, and can thus provide parallel access to intracranial lesions without the necessity of redetermining trajectories. Alternatively, bracket 251 could be a two part, hinged ring which snaps onto and around secondary plate member 212.

It is to be understood that the invention is not limited to the exact details of construction, operation, exact materials, or embodiment shown and described as obvious modifications and equivalents will be apparent to one skilled in the art; for example, a disk member rotatable about both an axis parallel and perpendicular to the secondary plate member could be utilized in lieu of the positioning ball. Accordingly, the invention is therefore to be limited only by the scope of the appended claims.

I claim:

1. A method for performing stereotactic surgery with a medical instrument upon a target within a skull, comprising the steps of:
   (a) establishing a first, predetermined geometric relationship between a positioning fixture attached to both the skull and to a support surface upon which the skull is disposed;
   (b) scanning the skull to produce an image of the target within the skull with respect to the positioning fixture;
   (c) transferring at least a portion of the positioning fixture to a phantom fixture and disposing the positioning fixture portion with respect to the phantom fixture to establish a second, predetermined geometric relationship therebetween, which is identical to the first, predetermined geometric relationship, whereby the slope of the skull where the positioning fixture is attached to the skull is duplicated within the phantom fixture;
   (d) disposing a phantom target within the phantom fixture at a location which corresponds to the location of the target within the skull;
   (e) determining the trajectory and distance of a medical instrument extending from the positioning fixture portion to the phantom target;
   (f) attaching the portion of the positioning fixture upon the skull in the same location it was originally attached to the skull; and
   (g) inserting the medical instrument through the positioning fixture in the trajectory determined from the phantom fixture, whereby the medical instrument will intersect the target in the skull.

2. The method of claim 1, wherein the positioning fixture is attached to the support surface by an attachment member having first and second end portions, and the first, predetermined geometric relationship is the attachment member disposed coplanar with the support surface; and the second, predetermined geometric relationship is the attachment member disposed coplanar with the phantom fixture.

3. The method of claim 2, including the steps of: moveably associating the first end portion of the attachment member with respect to the positioning fixture; and securing the attachment member with respect to the positioning fixture prior to scanning the skull.

4. The method of claim 3, including the steps of: moveably associating the attachment member with respect to a portion of the positioning fixture by using a positioning ball secured to the first end portion of the attachment member; and the positioning ball is rotatably received within the positioning fixture.

5. The method of claim 4, including the steps of using as the attachment member an elongate rod, which includes a means for identically orientating the second end portion of the attachment member with respect to both the support surface and the phantom fixture.

6. The method of claim 5, including the steps of: using a mating tongue and groove connection as the means for identically orientating the second end portion of the attachment member; and associating the mating tongue and groove connection with the second end of the attachment member and an end of an elongate rod disposed coplanar with the support surface and the phantom fixture.

7. The method of claim 1, including the steps of: using an outer and inner gimbal in the phantom fixture; and disposing the positioning fixture portion within the inner gimbal in the second geometric relationship.

8. The method of claim 7, wherein the positioning fixture is attached to the support surface by an attachment member having first and second end portions; the first, predetermined geometric relationship is the attachment member disposed coplanar with the support surface; the second geometric relationship is the attachment member disposed coplanar with the phantom fixture; and, while the positioning fixture portion is fixed with respect to the attachment member, the outer and inner gimbals are adjusted to receive the positioning fixture portion.

9. The method of claim 8, including the steps of locking the inner and outer gimbal with respect to the phantom fixture; securing the positioning fixture portion within the inner gimbal; and determining the trajectory and distance of the medical instrument by: inserting the medical instrument through the positioning fixture until it intersects the phantom target; and locking the medical instrument with respect to the positioning fixture at the desired trajectory and distance.

10. The method of claim 9, wherein the medical instrument is locked with respect to the positioning fixture portion by: associating a trajectory ball with the positioning fixture portion; inserting the medical instrument through the trajectory ball until it intersects the phantom target; and locking the trajectory ball with respect to the positioning fixture portion.

11. The method of claim 10, including the step of indicating the distance from the positioning fixture to the phantom target when the medical instrument has intersected the phantom target.

12. The method of claim 11, wherein the distance is indicated by associating a depth stop member with the medical instrument after the trajectory ball has been locked.

13. A system for performing stereotactic surgery with a medical instrument upon a target within a skull, comprising:
  (a) a positioning fixture, having associated therewith, a means for attaching the positioning fixture to both the skull and to a support surface upon which the skull is disposed; the positioning fixture including means for establishing a first, predetermined geometric relationship between the positioning fixture and the support surface; and
  (b) a phantom fixture, including: means for receiving at least a portion of the positioning fixture; means for establishing a second predetermined geometric relationship between the positioning fixture portion and the phantom fixture, wherein the second geometric relationship is identical to the first geometric relationship, whereby the slope of the skull where the positioning fixture is attached to the skull may be duplicated within the phantom fixture.

14. The system of claim 13, wherein the phantom fixture includes a phantom target which may be disposed within the phantom fixture at a location which corresponds to the location of the target within the skull with respect to the positioning fixture.

15. The system of claim 13, wherein the means for attaching the positioning fixture includes an attachment member having first and second end portions; in the first, predetermined geometric relationship, the attachment member is disposed coplanar with the support surface; and in the second, predetermined geometric relationship, the attachment member is disposed coplanar with the phantom fixture.

16. The system of claim 15, wherein the means for establishing the first, predetermined geometric relationship, includes the first end portion of the attachment member being moveably associated with respect to the positioning fixture; and the positioning fixture includes means for locking the attachment member with respect to at least a portion of the positioning fixture.

17. The system of claim 16, wherein the first end portion of the attachment member has a positioning ball associated therewith; and a portion of the positioning fixture includes means for rotatably receiving the positioning ball therein.

18. The system of claim 17, wherein the means for locking the attachment member with respect to a portion of the positioning fixture comprises at least one lock screw, which is associated with the rotatable receiving means, and is engageable with the positioning ball.

19. The system of claim 17, wherein the rotatable receiving means comprise a ball socket member which permits the first positioning ball to rotate therein; the ball socket member being rotatably mounted with respect to at least a portion of the positioning fixture and includes means for locking the ball socket member with respect to at least a portion of the positioning fixture.

20. The system of claim 19, wherein the ball socket member locking means comprises at least one thumb screw which contacts the ball socket member to lock its position with respect to a portion of the positioning fixture.

21. The system of claim 17, wherein the attachment member is an elongate rod having a means for identically orientating the second end portion of the attachment member with respect to both the support surface and the phantom fixture.

22. The system of claim 21, wherein the orientation means is a tongue and groove connection associated with the second end portion of the attachment member and both the support surface and the phantom fixture.

23. The system of claim 22, wherein the tongue and groove connection is associated with the support surface and the phantom fixture at an end of an elongate rod which is disposed coplanar with both the support surface and the phantom fixture.

24. The system of claim 13, wherein the means for establishing the second, predetermined geometric relationship, includes an inner and outer gimbal associated with the phantom fixture; the means for receiving at least a portion of the positioning fixture being associated with the inner gimbal.

25. The system of claim 24, wherein the means for receiving the positioning fixture portion includes means for locking the positioning fixture portion with respect to the inner gimbal.

26. The system of claim 24, wherein the phantom fixture includes means for locking the inner and outer gimbals with respect to the phantom fixture.

27. The system of claim 19, wherein the ball socket member has a trajectory ball disposed therein, upon the removal of the positioning ball.

28. The system of claim 27, wherein the second trajectory ball has a passageway therethrough adapted to permit a medical instrument to pass through the trajectory ball.

29. An apparatus, useful for performing stereotactic surgery, comprising:
 (a) a skull plate member, adapted to be secured to a skull;
 (b) a secondary plate member, adapted to overlie the skull plate member;
 (c) a ball socket member rotatably received within the secondary plate member;
 (d) means for aligning the skull plate member and secondary plate member with respect to one another; and
 (e) means for locking the ball socket member with respect to the secondary plate member.

30. The apparatus of claim 29, including a ball disposed within the ball socket member, the ball having an elongate attachment member secured thereto, the attachment member being adapted to be attached to an imaging table.

31. The apparatus of claim 30, including means for locking the ball within the ball socket member.

32. The apparatus of claim 29, wherein the ball socket member is an annular disk member having an upwardly extending cup-shaped flange member.

33. The apparatus of claim 32, wherein sections of the upwardly cup-shaped flange member are removed.

34. A phantom fixture, useful in performing stereotactic surgery, comprising:
 a frame;
 a pair of rotatable gimbals, the first gimbal being disposed within the frame and rotatable about a first axis; the second gimbal being disposed within the first gimbal and rotatable about a second axis, the first and second axis being perpendicular to one another; and
 the second gimbal including means for receiving at least a portion of a stereotactic positioning fixture.

35. A stanchion clamp, useful in performing stereotactic surgery, comprising:
 an elongate member having upper and lower ends;
 a bracket disposed at the lower end and including means for locking the bracket to at least a portion of a stereotactic positioning fixture; and
 means for securing a medical instrument to the elongate member, whereby stereotactic surgery procedures can be performed.

* * * * *